: (12) United States Patent
Schumacher et al.

(10) Patent No.: US 7,998,144 B2
(45) Date of Patent: Aug. 16, 2011

(54) SURGICAL INSTRUMENT AND OSTEOSYNTHESIS DEVICE

(75) Inventors: Joerg Schumacher, Tuttlingen (DE); Brian E. Dalton, Erie, PA (US); Ulrich Hahn, Rheinberg (DE)

(73) Assignee: Aesculap AG, Tuttlingen (DE)

( * ) Notice: Subject to any disclaimer, the term of this patent is extended or adjusted under 35 U.S.C. 154(b) by 692 days.

(21) Appl. No.: 11/644,546

(22) Filed: Dec. 22, 2006

(65) Prior Publication Data

US 2008/0154279 A1 Jun. 26, 2008

(51) Int. Cl.
*A61B 17/58* (2006.01)
*A61B 17/60* (2006.01)
*A61F 2/00* (2006.01)

(52) U.S. Cl. ............ 606/99; 606/96; 606/100; 606/103; 606/104; 606/86 A

(58) Field of Classification Search ................ 606/86 A, 606/103, 104, 264–279, 300–321, 96, 99, 606/100
See application file for complete search history.

(56) References Cited

U.S. PATENT DOCUMENTS

| | | | |
|---|---|---|---|
| 6,530,929 B1 | 3/2003 | Justis et al. | |
| 6,929,606 B2 | 8/2005 | Ritland | |
| 6,964,665 B2 | 11/2005 | Thomas et al. | |
| 7,008,422 B2 | 3/2006 | Foley et al. | |
| 2004/0158260 A1 | 8/2004 | Blau et al. | |
| 2004/0215190 A1* | 10/2004 | Nguyen et al. | 606/61 |
| 2005/0131422 A1 | 6/2005 | Anderson et al. | |
| 2005/0154389 A1 | 7/2005 | Selover et al. | |
| 2005/0159757 A1 | 7/2005 | Shluzas et al. | |
| 2005/0192589 A1 | 9/2005 | Raymond et al. | |
| 2005/0228400 A1 | 10/2005 | Chao et al. | |
| 2005/0245928 A1 | 11/2005 | Colleran et al. | |
| 2007/0173831 A1* | 7/2007 | Abdou | 606/61 |

FOREIGN PATENT DOCUMENTS

| | | |
|---|---|---|
| EP | 1 413 257 B1 | 4/2004 |
| EP | 1 523 950 A1 | 4/2005 |
| WO | WO 2004/004549 A2 | 1/2004 |
| WO | WO 2005/018490 A2 | 3/2005 |
| WO | WO 2005/037065 A2 | 4/2005 |
| WO | WO 2005/041799 A1 | 5/2005 |
| WO | WO 2005/058386 A1 | 6/2005 |
| WO | WO 2005/092218 A1 | 10/2005 |
| WO | WO 2006/029373 A1 | 3/2006 |
| WO | WO 2006/052504 A2 | 5/2006 |

* cited by examiner

*Primary Examiner* — Eduardo C Robert
*Assistant Examiner* — Christina Negrelli
(74) *Attorney, Agent, or Firm* — RatnerPrestia

(57) ABSTRACT

A surgical instrument for holding and inserting a connection member of an osteosynthesis device into a retainer of a bone anchorage element comprises a distal end, a proximal end and a first connection portion at a distal end. The first connection portion comprises a connection member receptacle for receiving at least a portion of the connection member. The instrument further comprises a locking mechanism which is transferable from a release position, in which the instrument is releasable from the connection member, to a connection position, in which the instrument can be connected to the connection member. Moreover, an osteosynthesis device comprising at least two bone anchorage elements and at least a connection member is proposed, which further comprises a surgical instrument for holding and inserting the connection member into at least one retainer of the bone anchorage elements.

53 Claims, 13 Drawing Sheets

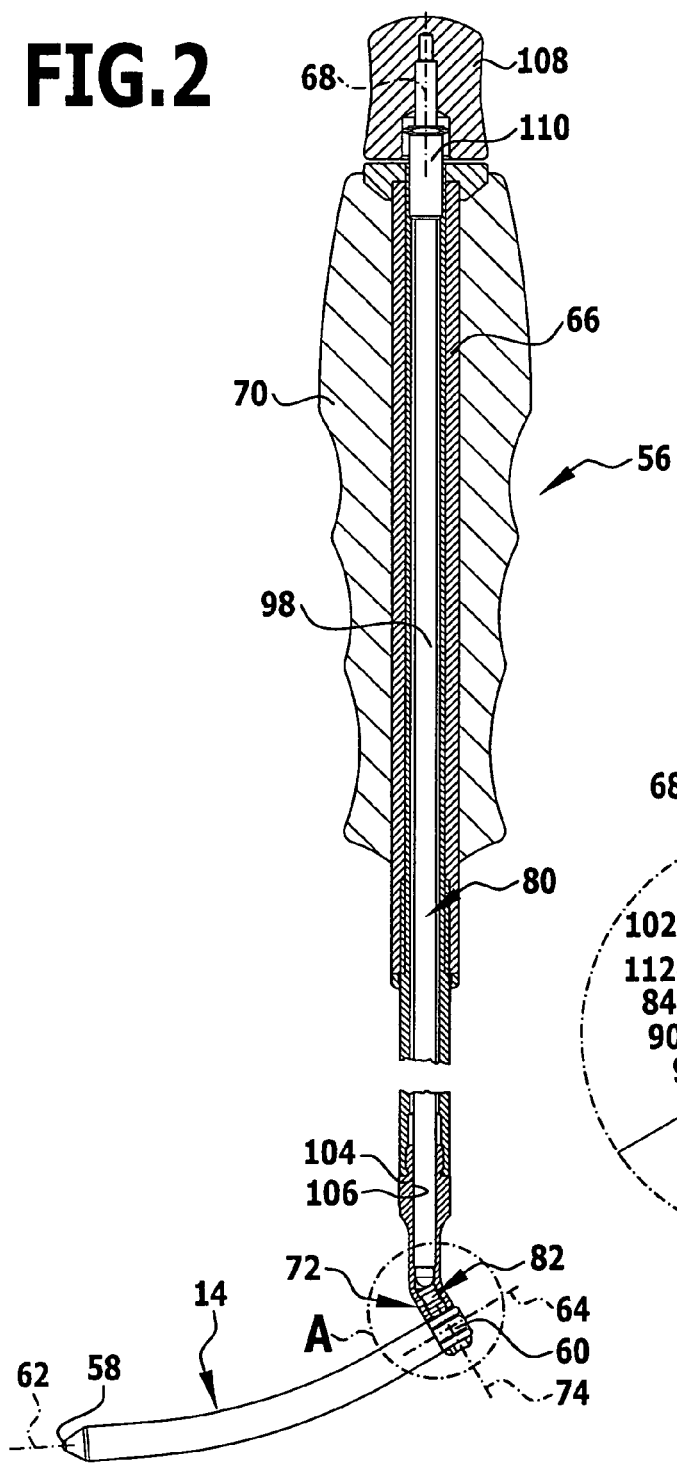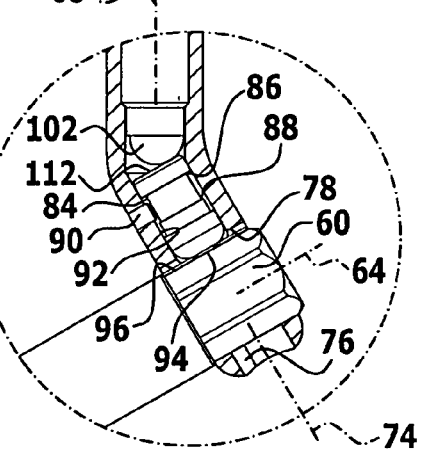

SURGICAL INSTRUMENT AND OSTEOSYNTHESIS DEVICE

FIELD OF THE INVENTION

The present invention relates to a surgical instrument for holding and inserting a connection member of an osteosynthesis device into a retainer of a bone anchorage element, the instrument comprising a distal end, a proximal end and a first connection portion at the distal end.

Furthermore, the present invention relates to an osteosynthesis device comprising at least two bone anchorage elements and at least one connection member, further comprising a surgical instrument for holding and inserting the connection member into a least one retainer of the bone anchorage elements, the instrument comprising a distal end, a proximal end and a first connection portion at the distal end.

BACKGROUND OF THE INVENTION

Osteosynthesis devices of the type described hereinabove are used, for example, to fasten two vertebrae of a human spinal column relative to each other, either because a vertebra is, damaged or because a disc connecting the two vertebrae is damaged. It is known that osteosynthesis devices comprise, for example, two bone screws with a U-shaped head in which a bone plate or an elongated rod is inserted and fixed by means of a fixation screw having external threads which correspond to internal threads provided on the head of the bone screw. However, it is difficult to insert a connection member, for example, a connection rod into a corresponding retainer of the bone anchorage element, in particular, if only a minimal invasive access is used for inserting and fixing the device to the spinal column in a desired manner. For example, forceps or a gripper are commonly used for holding and inserting the connection rod. However, it is not easy to apply a connection rod with such instruments since they are not specifically adapted for such purposes.

The object underlying the invention is, therefore, to improve a surgical instrument and an osteosynthesis device of the type described hereinabove in such a way that holding and inserting the connection member are easier.

SUMMARY OF THE INVENTION

In accordance with the invention, it is advantageous to provide a surgical instrument of the type described hereinabove wherein the first connection portion comprises a connection member receptacle for receiving at least a portion of the connection member, the instrument further comprising a locking mechanism which is transferable from a release position, in which the instrument is releasable from the connection member, to a connection position, in which the instrument can be connected to the connection member.

The surgical instrument according to the invention makes it possible to grasp the connection member when the instrument is in the release position and to lock or secure the instrument to the connection member by transferring the instrument from the release position to the connection position. In particular, a surgical instrument in accordance with the present invention offers the possibility that a person holding the instrument can release it without running the risk of losing the connection member inside or outside a human or animal body. The locking mechanism ensures that the connection member is securely held on the instrument when it assumes the connection position.

Holding the surgical instrument is particularly simple when the proximal end comprises a handle portion. Thus, a user can easily grasp the instrument with his hand on the handle portion.

In a preferred embodiment of the invention, the handle portion can have an ergonomically designed handle for improved grasping by a user, in particular, a surgeon or a surgical nurse.

It is advantageous for the instrument to be designed for torque proof connection with the connection member in the connection position. Such a construction allows turning of a connection member with the surgical instrument in a simple manner, which can be necessary for introducing a connection member or a part thereof into the retainer of the bone anchorage element. Moreover, it is thus possible to turn the connection member even when it is introduced into the retainer against a resistance of the retainer or the bone anchorage element or tissues surrounding the osteosynthesis device or the instrument.

It is expedient for the locking mechanism to comprise a locking member which is movably supported on the first connection portion. Thus, it is, in particular, possible to transfer the instrument from the release position to the connection position and vice versa by moving the locking member from a first position to a second position. In particular, the first and second positions can coincide with the release and locking positions.

In order to secure the locking member on the instrument, it is advantageous for at least one stop to be provided for limiting a movement of the locking member in distal direction. In addition, such a construction allows a most distal position of the locking member to be defined, for example, for limiting a force which is to be applied by the locking member to a connection member which is to be held with the instrument.

Moreover, it can be advantageous for at least one stop to be provided for limiting a movement of the locking member in proximal direction. Such a stop prevents, for example, a movement away from the connection member receptacle, which prevents loosening of the locking member from the instrument.

Preferably, the locking member is biased in proximal direction. In particular, when the locking member is supported on the instrument such that it is movable towards and away from the connection member receptacle, this design allows the instrument to be kept in a normal position defined by the release position.

The construction of the surgical instrument is, in particular, further simplified when a bias member is provided for biasing the locking member in proximal direction. In particular, the locking member can comprise the bias member, for example, the locking member and the bias member can be made from one piece.

In order to facilitate movement of the locking member, it is advantageous when a transmission member is provided for moving the locking member from the most proximal position to the most distal position. This allows, in particular, a remote movement of the locking member, for example, by actuating a handle portion of the instrument at a proximal end thereof.

In order that the surgical instrument can be easily used for minimal invasive surgery, it can also be expedient for a hollow shaft extending between the first connection portion and a proximal end to be provided. Further, a hollow shaft can also be used to house members of the instrument, for example, the transmission member and/or the locking member. In particular, the shaft allows protection of members which are, for instance, supported inside the shaft.

In order to further simplify the construction of the instrument, it is advantageous when the transmission member is movably supported on the shaft. It can be supported inside or outside the shaft.

In accordance with a preferred embodiment of the invention, an actuation member can be provided, which is arranged at the proximal end and is operatively connected with the locking member in such a way that actuation of the actuation member results in a movement of the locking member in a distal and/or proximal direction. Provision of such an actuation member simplifies the handling of the instrument. In particular, it is possible to move the locking member forward and backward by simple manipulation of the actuation member. This means that a user can transfer the instrument from the connection position to the release position and/or vice versa by simply actuating the actuation member.

In order to enable a simple transmission of an actuation force from the actuation member to the locking member, it is advantageous when the actuation member is operatively connected to the transmission member. This allows transfer of an actuation force from the actuation member via the transmission member to the locking member.

It can be expedient for the actuation member to be connected in a torque proof manner to the transmission member. Such a construction facilitates transmission of an actuation force, in particular, by turning the actuation member, for example, about a longitudinal axis thereof.

Preferably, the actuation member comprises a turning knob arranged at a proximal end of the instrument. A turning knob allows transmission of an actuation force directly or via a transmission member to the locking member by a simple rotation of the turning knob, for example, about a longitudinal axis thereof.

In order to increase the stability of the surgical instrument, it can be expedient for the transmission member to be rotatably supported on the instrument. Of course, the transmission member can also be supported on the instrument in such a way that a movement in a longitudinal direction is possible and/or easier.

Furthermore, it can be advantageous for the transmission member to be directly or indirectly threadingly engaged with the shaft or a part thereof. A threaded engagement of the transmission member and the shaft or a part thereof facilitates a defined movement of the transmission member relative to the shaft. In particular, it allows superposition of a rotary movement and an axial movement of the transmission member.

To allow a defined movement of the transmission member, it is advantageous for the transmission member to comprise a first threaded section, and for the shaft to comprise a second threaded section corresponding to the first threaded section for allowing a movement of the transmission member in distal or proximal direction in response to a turning movement of the transmission member about a longitudinal axis thereof.

In principle, it would be conceivable to provide the second threaded section at a proximal end of the shaft. However, in order to further increase the stability of the instrument, it is advantageous for the second threaded section to be provided in the form of an internal thread of the shaft in a section adjacent to the connection portion. Such a design, in comparison with a construction in which the threads are provided on a proximal end of the shaft, reduces bending forces.

In order to allow a simple transmission of an actuation force from the actuation member to the transmission member, it is expedient for the transmission member to comprise a proximal end, the actuation member being connected to the proximal end. This allows, in particular, transmission of an actuation force directly from the actuation member to the transmission member.

The design of the surgical instrument can be further simplified by the transmission member comprising a distal end, the distal end being engageable with the locking member.

A particularly simple construction of the surgical instrument is possible if the distal end of the transmission member abuts on a proximal end of the locking member. For example, such a construction allows transmission of an actuation force from the transmission member to the locking member by simply pushing the locking member with the transmission member in distal direction.

In order to allow manipulation of a curved connection member, for example, a curved rod, it can be advantageous for the transmission member to define a first longitudinal axis, for the locking member to define a second longitudinal axis and for the first longitudinal axis to be inclined relative to the second longitudinal axis. In particular, such a design makes it possible, for example, for a free tip of the connection member to be oriented transversely to the first longitudinal axis defined by the transmission member even if the connection member is curved. Thus, insertion of the connection member into a retainer of a bone anchorage element is noticeably simplified.

Preferably, an angle of inclination between the first and the second longitudinal axes lies in a range of from 100° to 170°. This allows, in particular, an angle of curvature between a first end and a second end of the connection member in the range of from 10° to 80°, with a free end of the connection member pointing in a direction transverse to the first longitudinal axis.

In order to further increase the stability of the surgical instrument, it can be expedient for the locking member to be guided in the distal end of the shaft.

It is beneficial for the locking member to comprise at least one abutment surface facing in distal and/or proximal direction. In particular, the at least one abutment surface allows definition of first and second positions of the locking member, for example, positions of the locking member when the instrument assumes the connection position and/or the release position.

The manufacture of the surgical instrument can be further simplified by the locking member comprising a peripheral groove and the at least one abutment surface being formed by side walls of the peripheral groove. Abutment surfaces constructed in such a manner can easily interact with a stop member projecting into the peripheral groove.

Preferably, the at least one stop comprises an inwardly pointing projection extending at least partially into the peripheral groove. In particular, the at least one stop can be arranged or supported on the shaft pointing towards a longitudinal axis defined by the shaft.

In order to reduce the number of pieces necessary for the manufacture of the surgical instrument, in can be advantageous for the transmission member to comprise a distal end, and for the distal end to comprise the locking member. In particular, this allows manufacture of the transmission member and the locking member from one piece.

In principle, it would be conceivable to design the connection member receptacle in the form of an open-ended wrench. In accordance with a preferred embodiment of the invention, however, the connection member receptacle comprises a through-hole for receiving the second portion of the connection member. Such a design ensures that the second connection portion of the connection member can only be released from the connection member receptacle in a direction parallel or substantially parallel to a longitudinal axis defined by the through-hole. Thus, a connection between the surgical instrument and a connection member is more stable than a connection between a connection member and an instrument which has a connection member receptacle in the form of an open-ended wrench.

Furthermore, it is expedient for the through-hole to be arranged in a direction transverse to a longitudinal axis defined by the instrument section on which the through-hole is arranged. Such a design prevents loss of the connection member if the instrument is moved parallel or generally parallel to a longitudinal axis defined by the instrument section on which the through-hole is arranged.

In order to allow application of torques from the instrument to the connection member, it is advantageous for the through-hole to have a cross section of a non-circular shape. Such a design allows rotation of the connection member about an axis defined by the connection member by means of the instrument without the risk that the connection member will not follow the movement of the instrument, which could be the case if the through-hole had a cross section of circular shape.

The construction of the instrument can be further simplified by the cross section being of polygonal shape. In particular, the cross section can be of hexagonal or octagonal shape, also with rounded edges like so-called Torx® tools.

Preferably, the instrument further comprises a connection member.

Advantageously, the connection member is designed in the form of a rod. A rod can be easily shaped in a desired manner.

Preferably, the connection member is curved. A curved connection member can be perfectly adapted to a curvature of the spinal column.

In principle, it would be conceivable to provide a connection member having a non-circular cross section. However, it is advantageous for the connection member to have a circular cross section. This allows insertion of the connection member into a retainer of a bone anchorage element in any desired rotational position.

According to a preferred embodiment of the present invention, the connection member has at least a second connection portion which is connectable with the first connection portion in the connection position. Provision of the at least one second connection portion facilitates a strong and stable connection of the connection member with the surgical instrument in the connection position.

Preferably, the at least one second connection portion is arranged at a first free end of the connection member. This allows handling of the connection member in a desired manner, in particular, insertion of a further free end of the connection member into a retainer of the bone anchorage element in an easy way.

Advantageously, the at least one second connection portion forms a first free end of the connection member. This simplifies the construction of the connection member noticeably.

In principle, it would be conceivable to provide a second connection portion having a circular cross section. However, in order to increase the stability of a connection between the connection member and the surgical instrument, it is advantageous for the at least one second connection portion to have a non-circular cross section. This allows, in particular, application of a torque with the instrument to the connection member without the risk that the connection member will not follow the movement of the surgical instrument.

The manufacture of the connection member can be further simplified by the at least one second connection portion having a polygonal cross section. In particular, in accordance with a preferred embodiment of the invention, the polygonal cross section of the second connection can be similar to or can have a shape corresponding to the connection portion receptacle.

It can be expedient for the at least one second connection portion to have a hexagonal cross section.

In accordance with a preferred embodiment of the invention, the at least one first and section connection portions are dimensioned such that they have play when the at least one second connection portion is inserted into the at least one first connection portion in the release position and that the play is eliminated in the locking position by means of the locking mechanism. Providing play in the release position makes insertion of the at least one second connection portion into the at least one first connection portion noticeably easier.

Preferably, the connection member has at least a second end which is designed in the form of an edge-free tip. Such a design reduces the risk of causing harm to tissues surrounding the spinal column to which the osteosynthesis device is to be applied.

In particular, the risk of harming tissues can be further reduced if the edge-free tip is blunt.

A surgeon can easily guide the connection member with the surgical instrument if the first longitudinal axis runs transversely to an axis defined by the at least one second end. In particular, this allows design of the surgical instrument and the connection member such that, for example, a longitudinal shaft of the instrument or the handle portion defines a longitudinal axis which runs transversely to the axis defined by the at least one second end. Furthermore, such a construction facilitates the use of the instrument, in particular, if the connection member is applied in minimal invasive surgery.

Of course, it would advantageous for the instrument to be able to be disassembled. If the instrument is able to be disassembled, it can be expedient for an irrigation adapter to be provided at the proximal end of the instrument, the adapter being connectable to an irrigation source by means of a hose or the like and being in fluid communication with the interior of the shaft. The irrigation adapter allows irrigation of the interior of the shaft in a simple way.

It is expedient for a reference element to be provided on the instrument, the reference element being constructed such that it is detectable by a detection device of a navigation system. Provision of such a reference element allows detection of the position and/or the orientation of the instrument, preferably in a three-dimensional space like an operating theatre. The navigation system can be, in particular, of the type using electromagnetic radiation for transmitting signals from the reference element to the navigation system and/or vice versa. Moreover, the reference element can be of the type comprising one or more marker elements which are either so-called passive or active markers. Passive markers do not emit radiation of any kind, in particular, electromagnetic waves or ultrasound or the like, actively but merely are designed for reflecting radiation or disturbing an electromagnetic field established in space. Active marker elements can be constructed so as to be able to emit radiation of the types mentioned above. The detection device of the navigation system is preferably of the type for detection of radiation or changes in electromagnetic fields.

It would be conceivable for the reference element to be unreleasably connected to the instrument. However, in order to facilitate cleaning and preparing of the instrument for navigation systems of different types, it is advantageous for the reference element to be releasably connectable to the instrument. This allows an easy exchange of reference elements as required. Furthermore, a reference element which is not required can be easily disassembled from the instrument.

Furthermore, the object postulated hereinabove is achieved by an osteosynthesis device comprising at least two bone anchorage elements and at least one connection member, further comprising a surgical instrument for holding and inserting the connection member into at least one retainer of the bone anchorage elements, the instrument comprising a distal end, a proximal end and a first connection portion at the distal end, the first connection portion comprising a connection member receptacle for receiving at least a portion of the connection member, the instrument further comprising a locking mechanism which is transferable from a release position, in which the instrument is releasable from the connection member to a connection position, in which the instrument can be connected to the connection member.

Such an improved osteosynthesis device can be easily applied to a spinal column. In particular, insertion of the connection member into the retainer of the bone anchorage element is greatly simplified.

Preferably, the at least two bone anchorage elements comprise at least one bone screw having a U-shaped receptacle for receiving at least a part of the at least one connection member, the at least one bone screw comprising a fixing element for securing the at least one connection member in the receptacle in a connection position. A connection member, in particular, a connection member in the form of a rod, can be easily inserted into a U-shaped receptacle. Furthermore, such a rod or a rod portion of a connection plate can be fixed to the anchorage element in a desired relation by means of the fixing element. The fixing element can, for example, be designed in the form of a fixing screw.

In accordance with a preferred embodiment of the invention the surgical instrument is formed by one of the instruments described hereinabove or defined by the claims.

BRIEF DESCRIPTION OF THE DRAWINGS

Further objects and advantages of the present invention appear hereinafter in the following description and claims. The accompanying drawings show, for the purpose of exemplification, without limiting the invention or the appended claims, certain practical embodiments of the present invention, wherein:

FIG. 2 is a longitudinal sectional view of a first instrument for holding and inserting a connection member;

FIG. 3 is an enlarged view of the area A in FIG. 2;

DETAILED DESCRIPTION OF THE INVENTION

Figure 1:
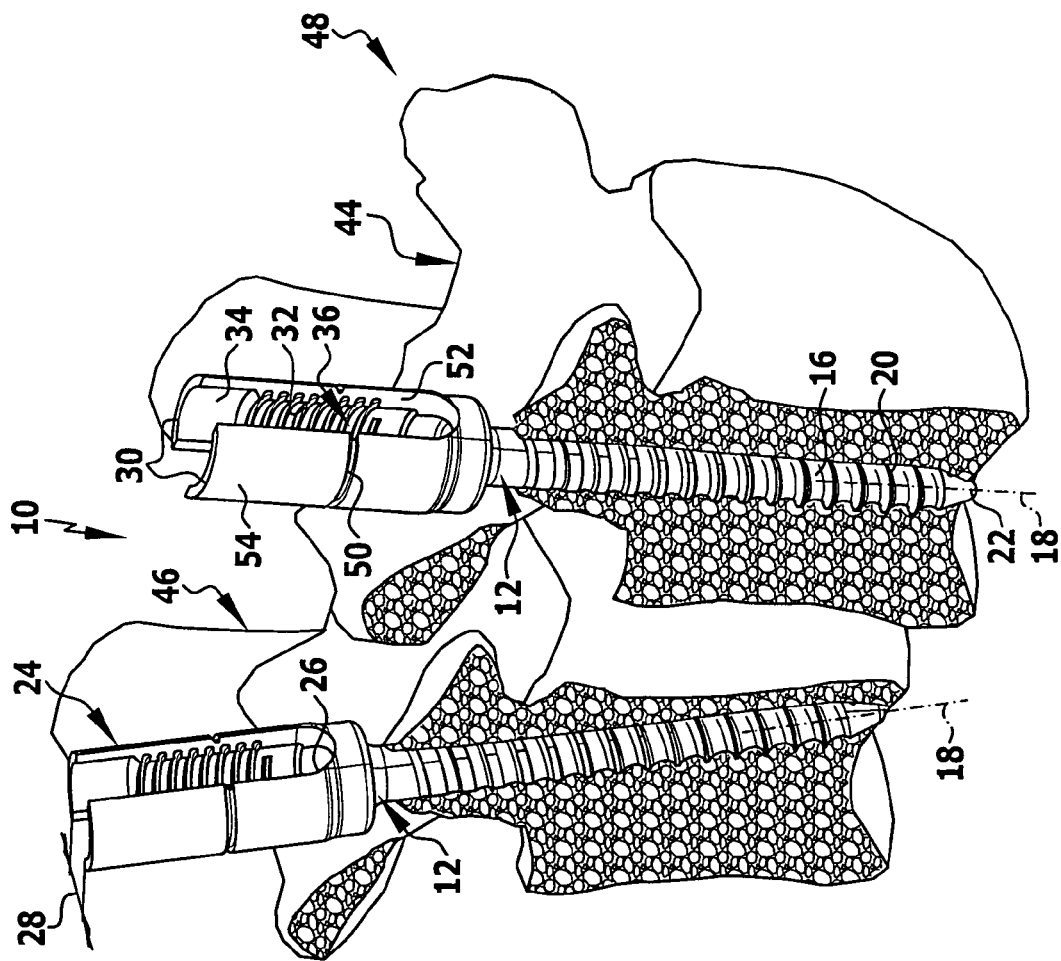
FIG. 1 is a sectional perspective view showing two bone anchorage elements fixed to two adjacent vertebrae.
Figure 4:
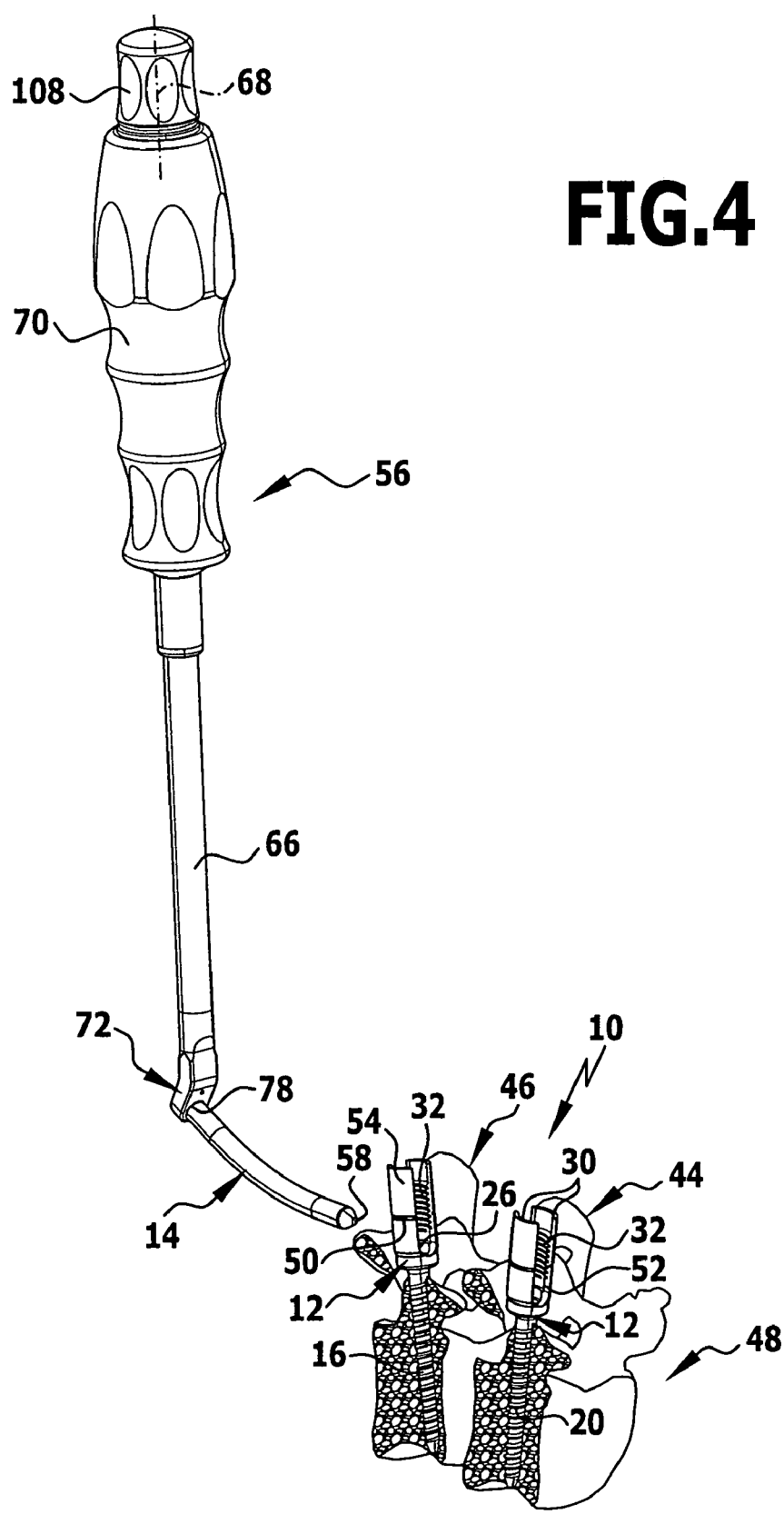
FIG. 4 is a perspective view of the first surgical instrument shown in FIG. 2 while inserting a connection member into retainers of the bone anchorage elements shown in FIG. 1.

An osteosynthesis device 10 shown in the figures comprises at least two bone anchorage elements in the form of pedicle screws 12 and at least one connection member in the form of a curved rod 14 having a substantially circular cross section.

Each pedicle screw 12 comprises an elongated threaded shaft 16 defining a longitudinal axis 18. Threads 20 provided on the shaft 16 can be provided in the form of self-cutting threads. A distal end of the shaft 16 forms a screw tip 22. A proximal end of the pedicle screw 12 forms a bone anchorage element head in the form of U-shaped head or a fork head 24. The fork head 24 is substantially sleeve-shaped and comprises a slot 26 which serves as a connection member seating and can also be called a retainer or a connection member receptacle in which a connection member, for example, a rod 14 or a plate-like element having at least one rod-shaped section, can be seated. The slot 26 has the shape of a semicircle at its closed proximal end with a curvature that matches an outer diameter of the rod 14. In like manner, a width 28 of the slot 26 corresponds approximately to the width or outer diameter of the rod 14. The fork head 24, due to its U-shaped design, comprises two legs having the form of a portion of a cylindrical side wall. Internal threads 32 provided on internal surfaces 34 of the legs 30 define a threaded section 36 to which external threads 38 of a fixation screw 40 correspond so that the fixation screw 40 can be screwed into the threaded section 36 by engaging the external threads 38 in the threads 32 and turning the fixation screw 40 clockwise about the longitudinal axis 18 in distal direction. The fixation screw 40 is designed in the form of a socket screw having a tool-engaging member in the form of a recess 42 which has a hexagonal cross section.

The pedicle screws 12 are screwed into vertebrae 44 and 46 of the spinal column 48 of a human or animal body as, for example, shown in FIG. 1. The legs 30 of the fork head 24 are longer than an external diameter of the rod 14, namely about three to four times longer. This allows simple insertion of the rod 14 into the slot 26. In order to reduce the height of the fork head 24, a predetermined breaking point in the form of a peripheral groove 50 is provided. The groove 50 separates a lower head portion 52 and upper head portion in the form of two tabs 54 defining free ends of the legs 30. The groove 50 is further arranged such that the internal threads 32 are partially provided on the lower head portion 52 and on the tabs 54. After insertion of the rod 14 into the slot 26 the tabs 54 can simply be broken away in a defined manner because of the groove 50.

The rod 14 can be inserted by a surgeon either by hand or by means of a rod insertion instrument 56. The rod 14 is curved with a first free end in the form of a blunt tip 58 and a second free end 60 having a multi-sided shape with a polygonal cross section, preferably a hexagonal or octagonal cross section. The rod 14 is slightly curved so that longitudinal axes 62 and 64 defined by the tip 58 and the end 60 are inclined relative to each other about an angle of about 25°.

The rod insertion instrument 56 comprises an elongated hollow shaft 66 defining a longitudinal axis 68. A proximal end of the shaft 66 is surrounded by an ergonomically designed handle portion 70 which allows an ergonomic grasping of the instrument 56 by a surgeon or a surgical nurse. A distal end of the shaft 66 defines a first connection portion 72 which defines a further longitudinal axis 74, which is inclined relative to the longitudinal axis 68 about an angle of about 30°. The first connection portion 72 has an opening 76 which is opened in distal direction and arranged concentrically about the longitudinal axis 74. In a direction transverse in relation to the longitudinal axis 74 the first connection portion is provided with a through-hole 78 which forms a connection member receptacle for receiving at least a portion of the rod 14, for example, the rod's end 60. The through-hole 78 is of internal multi-sided shape. Inner edges of the through-hole 78 can be rounded so that the through-hole 78 assumes the shape of a so-called Torx® tool. The through-hole 78 is dimensioned such that the end 60 can be inserted into the through-hole 78 parallel to its longitudinal axis 64, i.e. in a direction transverse to the longitudinal axis 74. Outer dimensions of the end 60 do not exactly correspond to the dimensions of the through-hole. Preferably, there is a small amount of play between the end 60 and the through-hole 78 when the end 60 is inserted in the through-hole 78.

In order to secure the rod 14 on the instrument 56 provision is made for a locking mechanism 80 to be arranged on the instrument 56. The locking mechanism 80 comprises a locking member 82 which is movably supported on the shaft 66. The length of the locking member 82 corresponds to about half of the length of the first connection portion 72. The locking member 82 is of substantially cylindrical shape having a peripheral groove 84 which defines circular stop surfaces 86 and 88 pointing in distal and proximal direction. A stop member 90 is arranged on the first connection portion 72 such that it projects at least partially from an internal side wall 92 of the first connection portion 72 into the groove 84. The stop member 90 can, in particular, be formed by a set screw having an outer diameter which is smaller than a width of the groove 84 parallel to the longitudinal axis 74. This allows the locking member 82 to move or to be moved from the most distal position, in which the stop surface 86 pointing in distal direction abuts on the stop member 90, to a most proximal position, in which the stop surface 88 pointing in proximal direction abuts on the stop member 90.

Although not shown in the figures, the locking member 82 can be biased in proximal direction by means of a bias member, for example, a spring. This results in a constrained movement of the locking member 82 in proximal direction. Such a bias member constrains the locking member 82 to assume its most proximal position which, thus, defines a normal position of the locking mechanism 80 or the instrument 56. In the normal position, a distal end surface 94 of the locking member 82 does not project into the through-hole 78. However, the end surface 94 can be forced in distal direction to abut on a surface 96 of the end 60 to key clamp the end 60 on the first connection portion 72, i.e., the instrument 56 then assumes a connection position. If the locking member 82 is moved in proximal direction, the side surface 96 and the end surface 94 disengage so that the end 60 can be released from the first connection portion 72, i.e. the instrument 56 then assumes a release position.

The locking mechanism 80 further comprises a transmission member 98 in the form of an elongated cylindrical rod which is provided with a short section of external threads 100 in the region of its distal end 102. The distal end 102 has substantially the form of a semisphere. An inner section of the shaft 66 next to the first connection portion 72 is provided with internal threads 106 which correspond to the external threads 104. A proximal end of the transmission member 98 extends beyond a proximal end of the handle portion 70 and is connected in a torque proof manner to an actuation member in the form of a knob 108. For guiding the transmission member, a so-called "luerlock" is provided on the proximal end of the shaft 66 and extends at least partially in proximal direction beyond the handle portion 70. The "luerlock" forms a standard irrigation adapter which can be connected to an irrigation source, for example, by means of a hose or the like and which is in fluid communication with the interior of the shaft 66. The adapter 110 facilitates cleaning of the instrument 56 after disassembling the transmission member 98.

The transmission member 98 can be inserted into the shaft 66 by inserting the end 102 through the adapter 110 into the interior of the shaft 66 until the threads 106 enter into contact with the threads 104. Then, a further axial movement of the transmission member 98 in distal direction requires a turning movement of the transmission member 98 about the longitudinal axis 68 clockwise so that the end 102 proceeds towards a proximal end 112 of the locking member 82. As soon as the end 102 gets into contact with the proximal end surface 112 pointing in proximal direction, further movement of the transmission member 98 in distal direction urges the locking member 82 in distal direction and allows clamping of the end 60 in the through-hole 78. Thus, turning the knob 108 allows transfer of the instrument 56 from the release position, in which the end 60 can be introduced into the through-hole 78 and retracted therefrom, to a connection position, in which the end 60 is securely held in the through-hole 78 in a clamped manner. A connection position of the instrument 56 is shown, in particular, in FIGS. 2 and 3.

Figure 5:
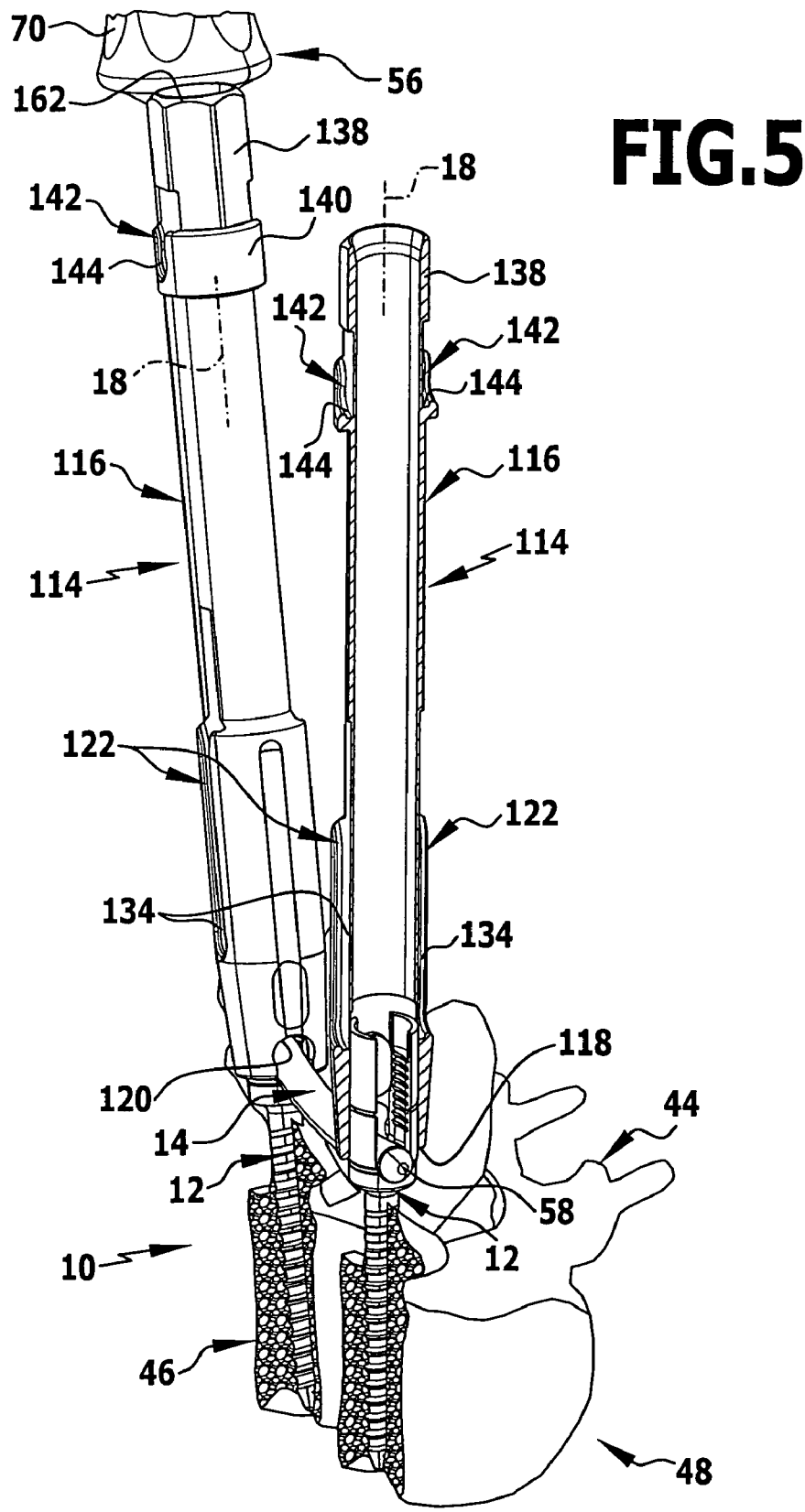
FIG. 5 is a partially sectional perspective view of a connection member inserted into a retainer of the bone anchorage elements and held with the first instrument.
Figure 6:
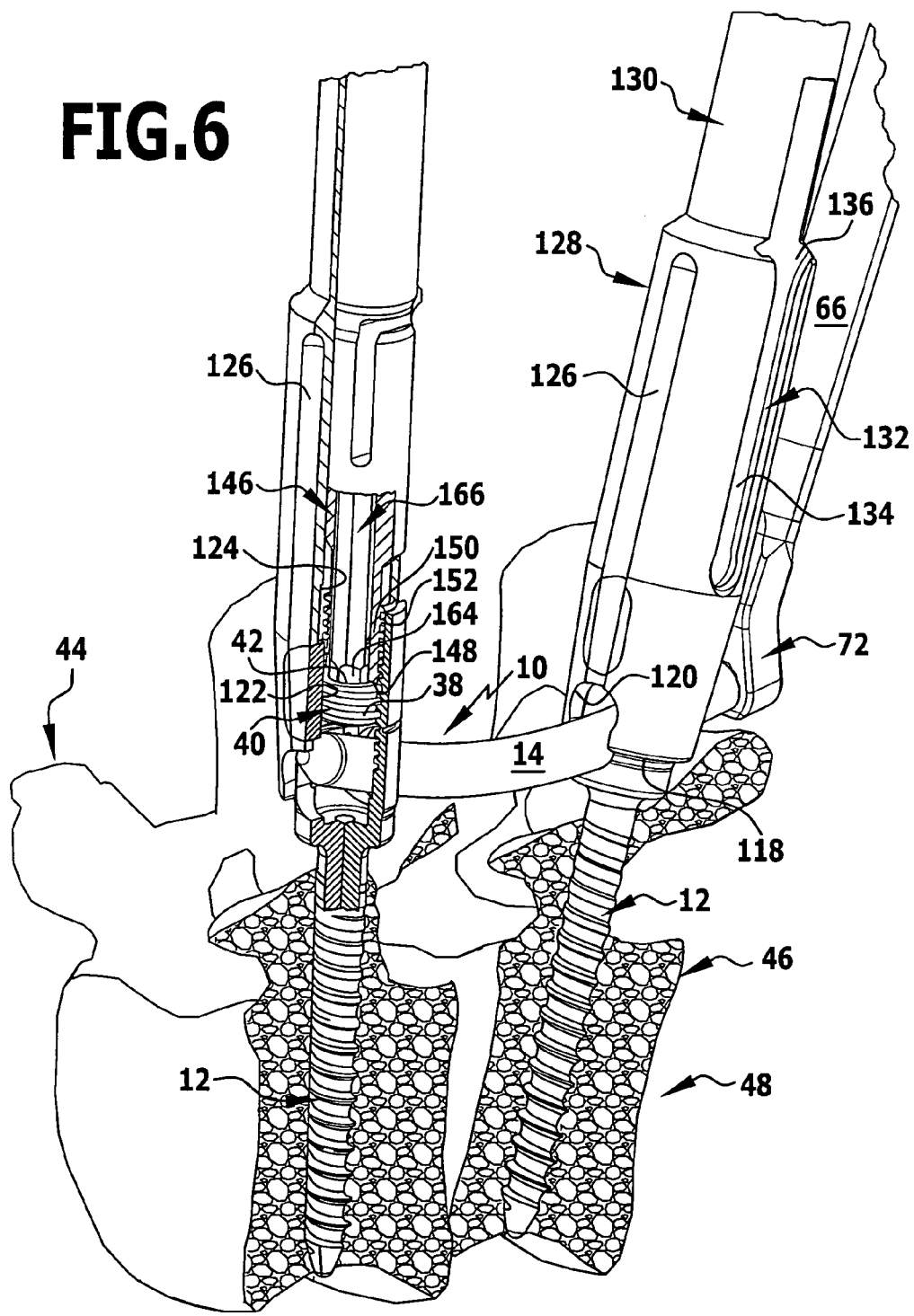
FIG. 6 is a partially sectional perspective view of the scenario shown in FIG. 5 further showing second instruments for applying fixing screws to the retainers of the bone anchorage elements.

When the rod 14 is securely held on the instrument 56 in the connection position, a surgeon can easily introduce the curved rod 14 into the slots 26 of the fork heads 24 of the pedicle screws 12. It is even possible to apply a torque to the rod 14 by means of the instrument 56, which facilitates insertion of the rod into the patient's body and through surrounding tissues towards and into the slots 26. After insertion of the rod 14 into the slots 26 with the instrument 56 the rod is held in the desired position by means of the instruments as shown in FIGS. 5 and 6.

In a next step a further surgical instrument 114 is used for guiding the fixation screw 40 into the fork head 24 and screwing in the fixation screw 26 for fixing the rod 14 to the fork head 24 of the pedicle screw 12. The surgical instrument 114 comprises a longitudinally extending tubular outer sleeve 116 which can be connected to the fork head 24 in such a way that a longitudinal axis 18 defined by the sleeve 116 coincides with the longitudinal axis 18 of the screw 12. Two insertion recesses 120 extending from a distal end 118 of the sleeve 116 in proximal direction are provided symmetrically and in diametrically opposed arrangement in relation to the longitudinal axis 18. The insertion recesses 120 are dimensioned such that they are adapted to receive the rod 14 and to form a proximal stop effective in proximal direction for the rod 14.

In order to facilitate alignment of the insertion recesses 120 and the slots 26, two first guide members 122 are provided on the sleeve 116. The guide members 122 are inserted in a side wall of the sleeve 116 and protrude beyond an inner wall surface 124 of the sleeve 116 so that they can engage the slots 26 when the sleeve 116 is moved over the fork head 24 in distal direction. The first guide members 122 are arranged in the vicinity of the insertion recesses 120 but proximal thereof. As can be seen, for example, in FIG. 6, the first guide members 122 engage the slots 126 between the tabs 54. On the exterior of the sleeve 116 two shallow grooves 126 are provided which extend from the insertion recess 120 parallel to the longitudinal axis 18 in proximal direction over a length which corresponds substantially to the length of a distal end portion 128 of the sleeve 160. The distal end portion 128 has a larger diameter than a sleeve-like centre portion 130 of the sleeve 116 which extends in proximal direction starting from the distal end portion 128. The distal end portion 128 further comprises two distractor-engaging portions 132 in the form of undercut grooves 134 having a cross-sectional shape in the form of a T. A distal end of the groove 134 is closed, whereas a proximal end of the groove 134 is provided with an insertion opening 136. The grooves 134 extend parallel to the longitudinal axis 18 over a length defined by a distance between a transition region, defined between the distal end portion 128 and the centre portion 130, and proximal ends of the first guide members 122. The grooves 134 are arranged diametrically opposed in relation to the longitudinal axis 18 but displaced about an angle of rotation of 90° with respect to the insertion recesses 120.

Figure 8:
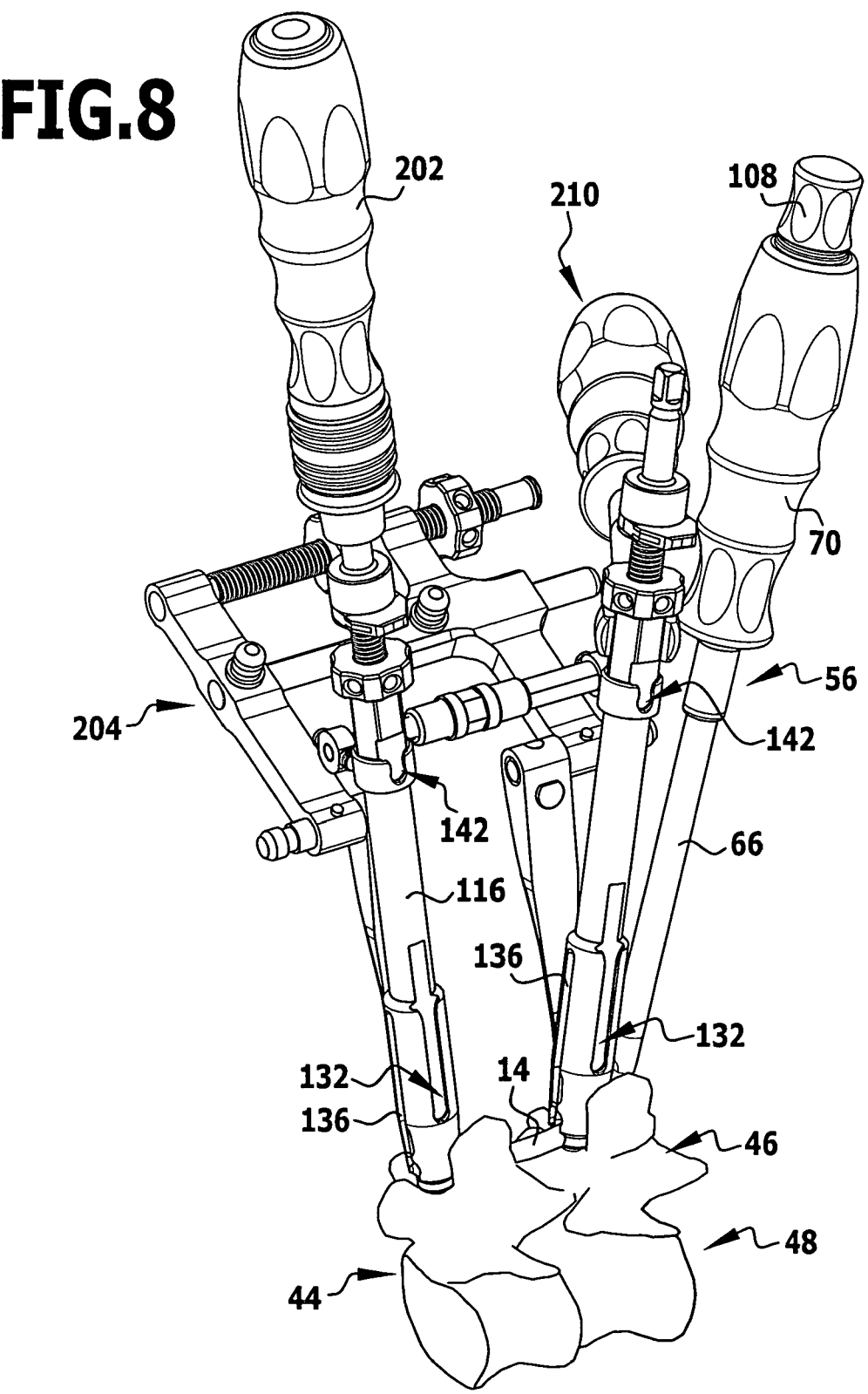
FIG. 8 is a perspective front elevational view of an osteosynthesis device applied by means of first and second surgical instruments connected to a distractor for positioning the vertebrae in a desired relative position.
Figure 9:
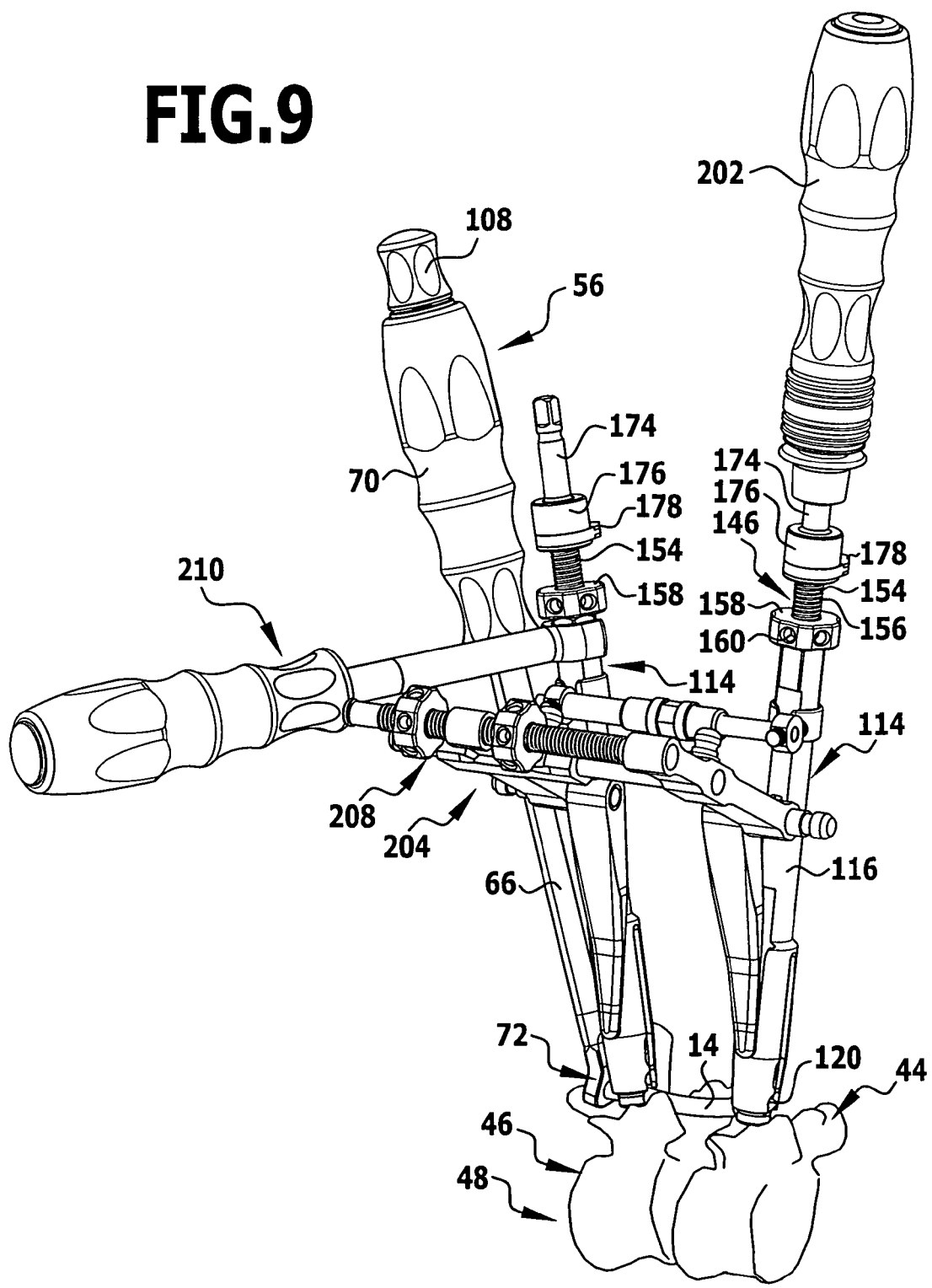
FIG. 9 is a back perspective elevational view of the arrangement shown in FIG. 8.
Figure 10:
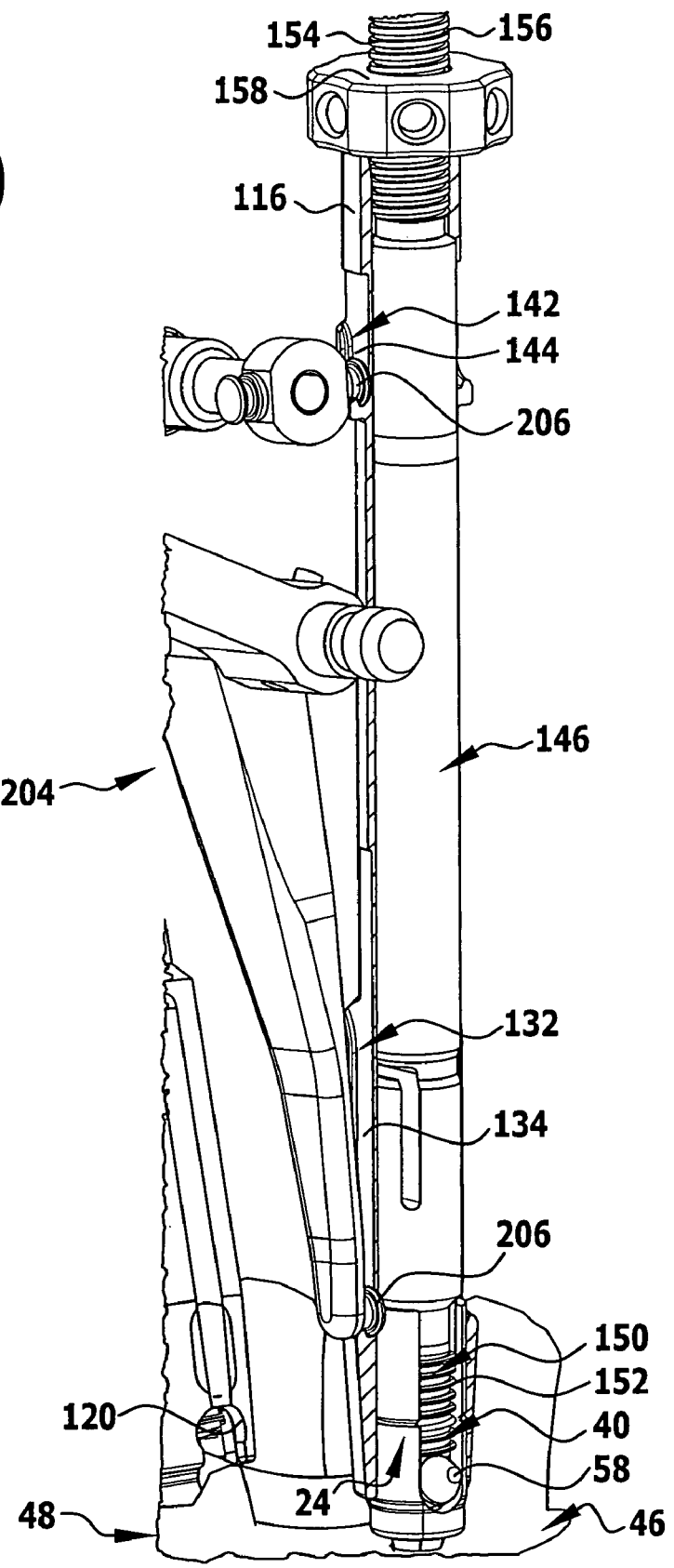
FIG. 10 is a partially sectional perspective view of one of the second instruments showing the connection of the second instrument to the distractor.
Figure 11:
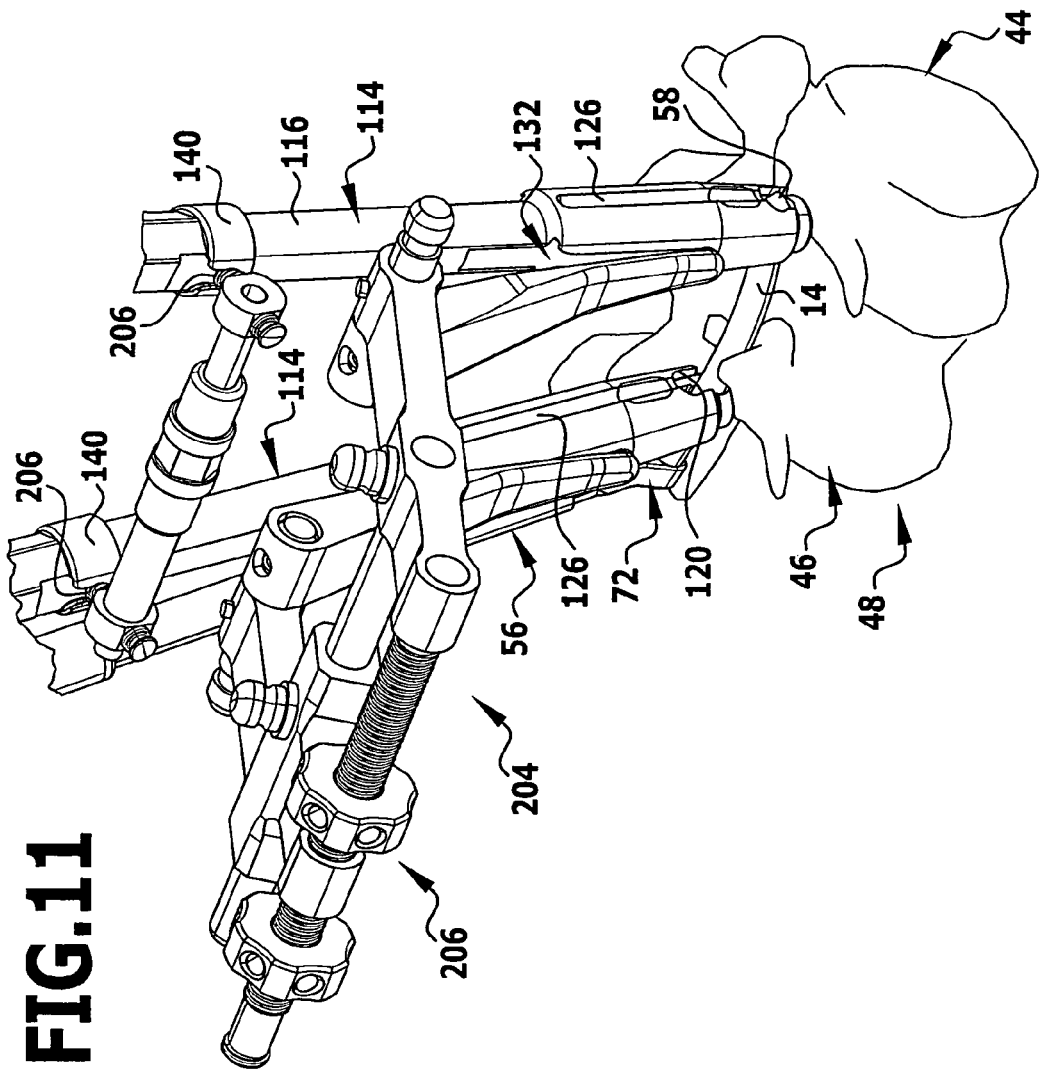
FIG. 11 is an enlarged back perspective view of the distractor shown in FIGS. 8 through 10.
Figure 12:
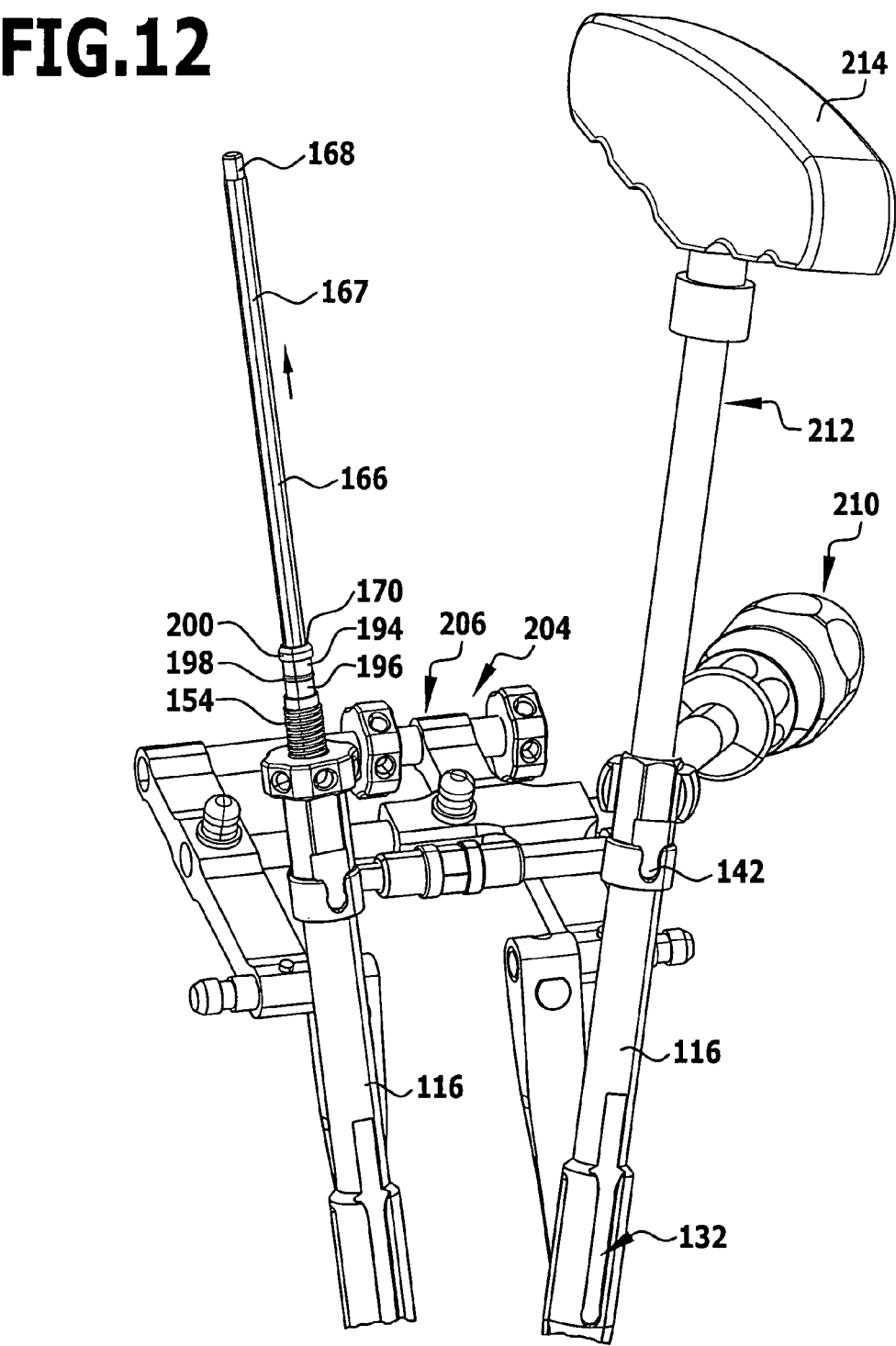
FIG. 12 is a front perspective elevational view taken while tightening the fixing screws with a torque wrench.
Figure 13:
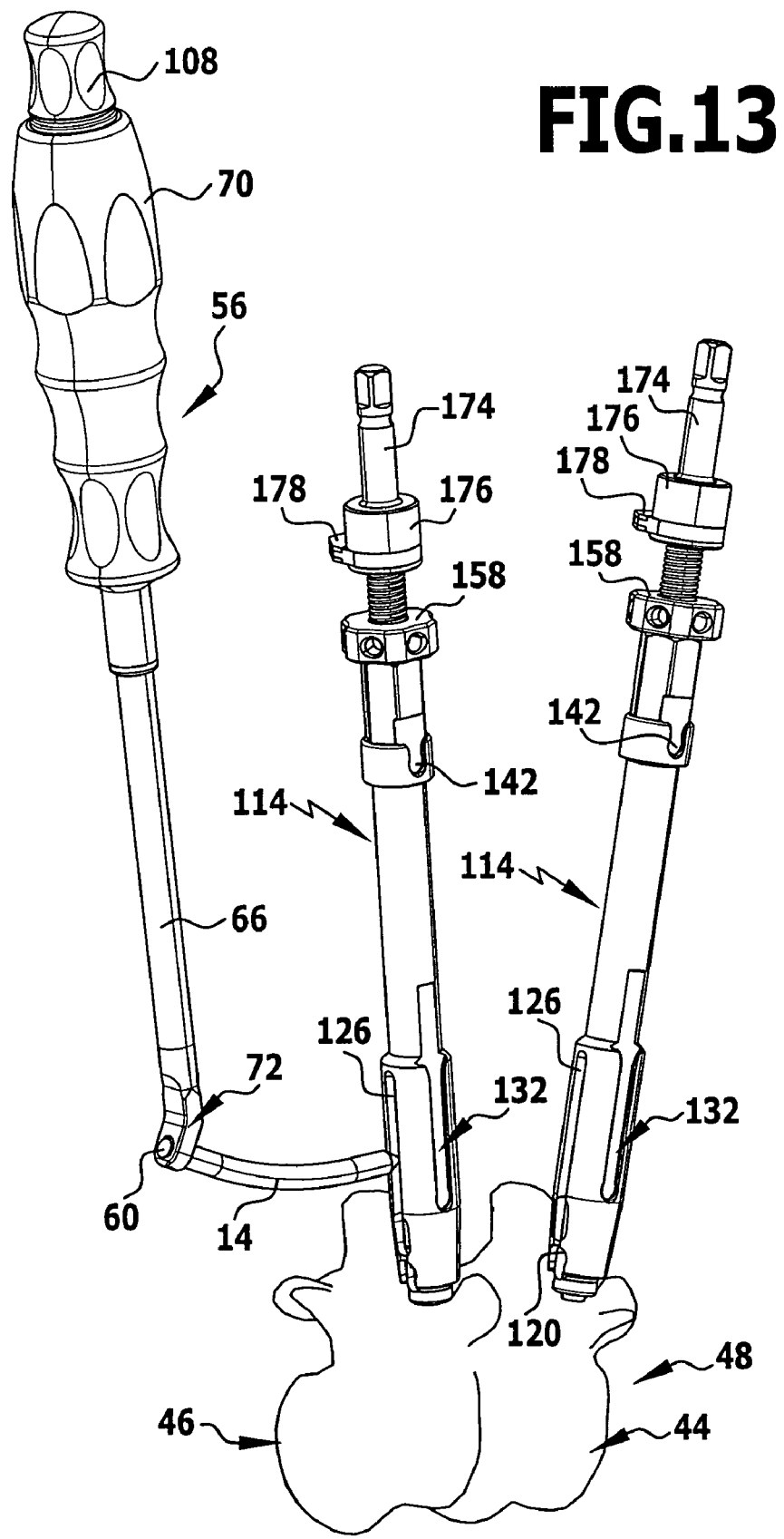
FIG. 13 is a perspective view of the osteosynthesis device taken while inserting the connection member with the first instrument into the retainers of the bone anchorage elements with the second instruments already connected to the bone anchorage elements.

A proximal end of the sleeve 116 has an external non-circular cross section of polygonal shape, namely of hexagonal shape. It forms an end portion 138 of multi-sided shape which can be engaged by an open-ended wrench, for example, a wrench 210 as shown in FIGS. 8, 9 and 12.

On a distal side of the end portion 138 the outer diameter of the sleeve 116 increases in one step and forms a ring-like peripheral projection 140. Second guide members 142 are provided on the projection 140 in the form of two undercut grooves 144 which are closed in distal direction and open in proximal direction. The grooves 144 extend parallel to the longitudinal axis 18 and are aligned with corresponding grooves 134 forming the first guide member 122.

The surgical instrument 114 further comprises a first hollow shaft 146 which is dimensioned such that it can be introduced into the sleeve 116 through the end portion 138. A distal end 148 of the shaft 146 is provided with an externally threaded section 150 comprising threads 152 which correspond to the external threads 38 of the fixation screw 40. Consequently, the threads 152 also correspond to the internal threads 32 of the fork head 24. After insertion of the shaft 146 into the sleeve 116 the externally threaded section 150 can be threadingly engaged with the threads 32. The externally threaded section 152 forms a first tool member of the instrument 114. Moreover, the shaft 146 has a further externally threaded section 154 arranged in the region of its proximal end and comprising threads 156. A counter nut 158 is threadingly engaged with the externally threaded section 154. The counter nut 158 has a substantially hexagonal outer cross section with blind bores 160 whose longitudinal axes point radially away from the longitudinal axis 18. The counter nut 158 serves for clamping the sleeve 116 to the pedicle screws 12. For that purpose, a distal side surface of the nut is brought into contact with a proximal end surface 162 of the end portion 138. Further clockwise turning of the counter nut 158 clamps the sleeve 116 between the counter nut 158 and the rod which is inserted into the slot 26 when the shaft 146 threadingly engages the fork head 24.

The surgical instrument 114 further comprises a second tool member 164 which is formed by a multi-sided end portion of an elongated shank 166. The second tool member 164 has an outer non-circular cross section of polygonal shape, preferably of hexagonal shape. The second tool member is designed to correspond to the recess 42 of the fixation screw 40. The shank 166 has a shaft-engaging portion 167 which also has a non-circular cross section of polygonal shape and extends almost over the entire length of the shank 166. The shank 166 has a length so that a proximal end 168 extends beyond a proximal end 170 of the shaft 146. The cross section of the shank 166 is preferably of hexagonal shape but can also be, as shown in FIG. 6, of octagonal shape. The shank 166 can be introduced into the shaft 146 through the end 170.

Since an inner cross section of the shaft 146 corresponds to the outer cross section of the shaft engaging portion 167 of the shank 166 the shank can be inserted into and moved relative to the shaft 146 parallel to the longitudinal axis 18. Moreover, the shank and the shaft are thus supported on the instrument 146 in a torque proof manner relative to each other. This means that a turning action applied to the shank 166 results in a constrained rotary movement of the shaft 146.

Furthermore, the shank 166 and the shaft 146 can be brought into and locked in a defined axial relation. For this purpose, a locking mechanism 172 is provided. The proximal end 168 is connected to a handle adapter 174 in a torque proof manner. The handle adapter 174 has a distal end portion 176 which surrounds a proximal end portion of the shaft 146 in a sleeve-like manner. The end 170 forms a stop for an internal circular surface pointing in distal direction of the handle adapter 174.

Figure 7:
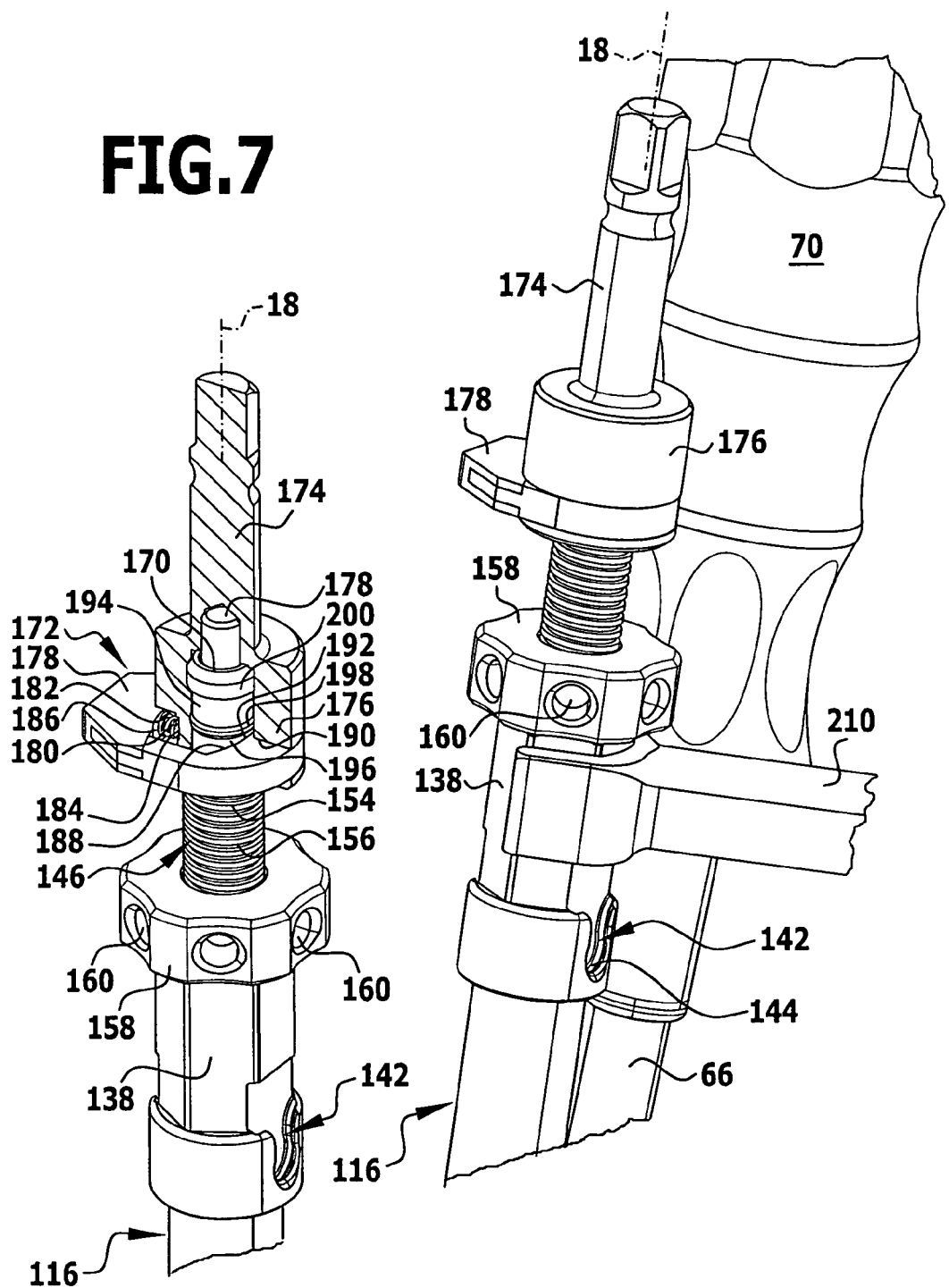
FIG. 7 is a partially sectional view of proximal ends of the second instruments which are partially shown in FIG. 6.

A first locking member 178 is supported on the end portion 176 and movable in a direction transverse to the longitudinal axis 18. The locking member 178 is designed substantially in the form of a push button, which is held in a locking position, as shown in FIG. 7, by means of a bias member in the form of a coil spring 180. The coil spring 180 is supported on the one hand on the bottom surface 180 of a blind bore 182 whose longitudinal axis extends transversely to the longitudinal axis 18. The coil spring 180 is supported on the other hand on an inner surface 186 of the locking member 178 pointing towards the longitudinal axis 18. The locking member 178 is provided with a through-hole 188 such that the substantially plate-like locking member 178 surrounds the shaft and engages a slot 190 of the end portion which is diametrically opposed to the side surface 186 which forms a portion of an inner wall of the through-hole 188. As a result of the design of the locking mechanism 172, the coil spring 180 pushes the side surface 186 away from the longitudinal axis 18, so that a side surface 192 of the through-hole 188 which is substantially diametrically opposed to the side surface 186, is moved towards the longitudinal axis 18. Due to the coil spring 180 the locking mechanism 172 assumes a locking position as a normal position.

For locking the shank 166 to the shaft 146, the shaft 146 is provided with two ring grooves 194 and 196 which are separated by a peripheral projection 198.

The ring groove 194 is arranged adjacent to a ring flange 200 which defines the proximal end 170 of the shaft 146. The projection 198 limits the ring groove 194 on a distal side and the ring groove 196 is arranged adjacent to the projection 198 on a distal side thereof. The ring grooves 194 and 196 form second locking members of the locking mechanism 172. Further, the ring groove 196 is limited distally by the externally threaded section 154.

A width of the ring grooves 194 and 196 parallel to the longitudinal axis 18 is a little bit larger than the thickness of the plate-like locking member so that the locking member 178, which is guided in the slot 190, can enter into contact with one of the two grooves 194 with its side surface 192. The shank 166 is secured on the shaft 146 when the locking member 178 engages one of the ring grooves 194 or 196. For disengaging, the shank 166 and the shaft 146, the locking member 178 has to be moved against the force exerted by the coil spring 180 so that the side surface 192 releases the ring groove 194 or 196.

The locking mechanism 172 is now in a release position, which allows withdrawal of the shank 166 in proximal direction.

The ring groove 196 defines a first locking position, in which the second tool member 164 extends beyond a distal end of the shaft 146. The ring groove 194 defines a second locking position, in which the shank 166 is retracted into the shaft 146 and brought out of engagement with the fixation screw 40 when the locking member 178 engages the ring groove 194.

The handle adapter 174 can be releasably connected to a handle 202, preferably in the form of ratchet. This allows an easy rotary movement of the shank 166 both clockwise and counter clockwise.

For applying the fixation screw 40 to the fork head 24, the instrument 114 is preassembled as follows. In a first step, the shank 166 is inserted into and locked to the shaft 146 in the first locking position, in which the second tool member 164 extends beyond the distal end 148. The fixation screw 40 is then connected to the second tool member 164 by introducing the same into the recess 42. Now, the shank 166 connected to the shaft 146 can be introduced together with the shaft 146 through the sleeve 116 and moved forward in distal direction until the external threads 38 of the fixation screw 40 contact the threads 132. Rotation of the handle 202 connected to the shank 166 threadingly engages both the fixation screw 40 and the externally threaded section 152 with the threaded section 36 of the fork head 24.

The pitch of the external threads 38 corresponds to the pitch of the threads 152 so that the fixation screw 40 cannot block the threaded engagement of the externally threaded section 150 and the threads 32. In order to facilitate the engagement of the threads 152 and the threads 32 after screwing in the fixation screw 40 into the fork head 24, the ring groove 196 is a little bit wider than the thickness of the locking member 178 parallel to the longitudinal axis 18 so that sufficient play is provided for leading a free end of the threads 152 into the threads 32. As described above, the screw 40 can be screwed in until it contacts the rod 14 inserted in the slot 26. Further turning of the shank 166 results in a pretightening action which secures the rod 14 to the pedicle screw 12. With a further second surgical instrument 114 the rod 14 can be secured to the pedicle screw 12 in the same way.

In order to position the vertebrae 44 and 46 in a desired position relative to each other, a distractor 204 is provided, which can be connected to the instruments 114 which are clampingly secured to the pedicle screws 12 as shown, for example, in FIGS. 8, 9, 11 and 12. For this purpose, the distractor 204 is provided with at least four adapters 206 which are identically designed in the form of plate-like projections which can be introduced into the distractor-engaging portions 132 and into the second guide members 142. The distractor 204 further comprises a drive mechanism 208 which allows adjustment of a distance between the adapters 206 which are engaged with the instruments 114 in such a way that a distance between the surgical instruments 114 and an inclination between the same can be adjusted in a desired manner. In particular, the distractor 204 can be used to move the vertebrae 44 and 46 away from each other to release pressure exerted on the spinal cord. The distractor 204 is substantially known in the art, however, the adapters 206 are new since grooves 134 and 144 on the sleeve 116 reduce a maximum diameter on the sleeve 116. This has the further advantage that a smaller access to the patient's body is required for introducing the instrument 114 into the body.

Further, a flat ended wrench 210 can be provided for engaging the end portion 138 of the sleeve, which allows turning of the sleeve 116 as a whole together with the pedicle screw 12 secured thereto.

When the vertebrae 44 and 46 are positioned as desired, the fixation screws 40 are pretightened such that the rod 14 is secured to the pedicle screws 12. The rod 14 is still connected to the instrument 56. In a next step, the locking mechanism 172 is transferred from the first locking position to the second locking position in which the second tool member 164 is retracted into the shaft 146. Now, the shank 166 and the shaft 146 are still locked relative to each other but assume the second locking position. This allows unscrewing of the shaft 146 from the fork head 24 without unscrewing the fixation screw 40 since the second tool member 164 and the recess 42 are disengaged. After unscrewing the shaft 146 from the fork head 24 the shaft 146 is retracted from the sleeve 116.

In a next step, the fixation screw 40 can be tightened with a defined torque by use of a torque wrench 212 whose distal end engages the recess 42 and which has a proximal end in the form of a T-bar 214. The T-bar can be grasped by hand and turned for fixing the fixation screw 40 into the fork head 24.

Afterwards, the torque wrench 212 is retracted and the locking mechanism 80 of the instrument 56 can be transferred from the connection position to the release position, which allows removal of the instrument 56 from the rod 14. Finally, the distractor 204 and the sleeves 116 are withdrawn from the fork heads 24.

Before closing the access to the patient's body, the tabs 54 of the pedicle screws 12 are broken off and removed from the patient's body.

The method for fixing the osteosynthesis device 10 on the vertebrae 44 and 46 of the spinal column 48 in a minimal invasive manner comprising the steps of minimal invasive accessing the spinal column, fixing a pedicle screw having a fork head 24 into each of the two vertebrae 44 and 46, inserting the rod 14 into the slots 26 by means of the instrument 56, threadingly engaging the fixation screw 40 with the fork head 24 by means of the instrument 114, tightening the fixation screws 40 for securing the rod 14 to the pedicle screws 12 and disengaging the instruments 56 and 114 from the rod 14 and the pedicle screws 12, can be at least partially modified.

Alternatively, the instrument 114 can be mounted on the pedicle screw 12 before screwing the pedicle screw 12 into one of the vertebrae 44 or 46. For preassembling the unit comprising the instrument 114, the pedicle screw 12 and the fixation screw 40, the sleeve is moved over the fork head 24 and a subunit comprising the shaft, the shank and the fixation screw preassembled as described above, is introduced into the sleeve 116. By means of the counter nut 158 the instrument 114 can be tightly clamped to the pedicle screw 12. Now, since the instrument 114 is connected to the pedicle screw 12 in a torque proof manner, the pedicle screw 12 can be screwed into the vertebrae 44 or 46 by means of the instrument 114. For this purpose, the instrument 114 can be, for instance, connected to the handle 202.

In a next step, the rod 14 has to be inserted into the slots 26 of the pedicle screw 12. The shallow grooves 126 on the sleeve 116 simply insertion of the rod 14 into the slot 26. The surgeon moves the rod 14 with its tip 58 towards the sleeve 116 in order to engage the tip 58 and the shallow groove 126. As soon as the tip 58 is guided in the shallow groove 126, the surgeon has only to move the instrument 56 parallel to the longitudinal axis 18 and the tip 58 is automatically guided into the recess 120. Now, the surgeon can move the instrument 56 transversely to its longitudinal axis 68, which moves the rod 14 into the slot 26. Pushing the rod 14 through the slot 26 moves the tip 58 out of the slot 26 on its other side and the surgeon can then manipulate the instrument 56 in such a way that the tip 58 engages the shallow groove 126 of the second sleeve 116 so as to introduce the tip 58 also through the recess 120 into the slot 26 of the other pedicle screw 12.

In a next step the rod 14 can be pretightened by means of the fixation screw 40 in the above-described manner. The further procedure for fixing the osteosynthesis device to the spinal column 48 corresponds to the method described above.

Figure 14:
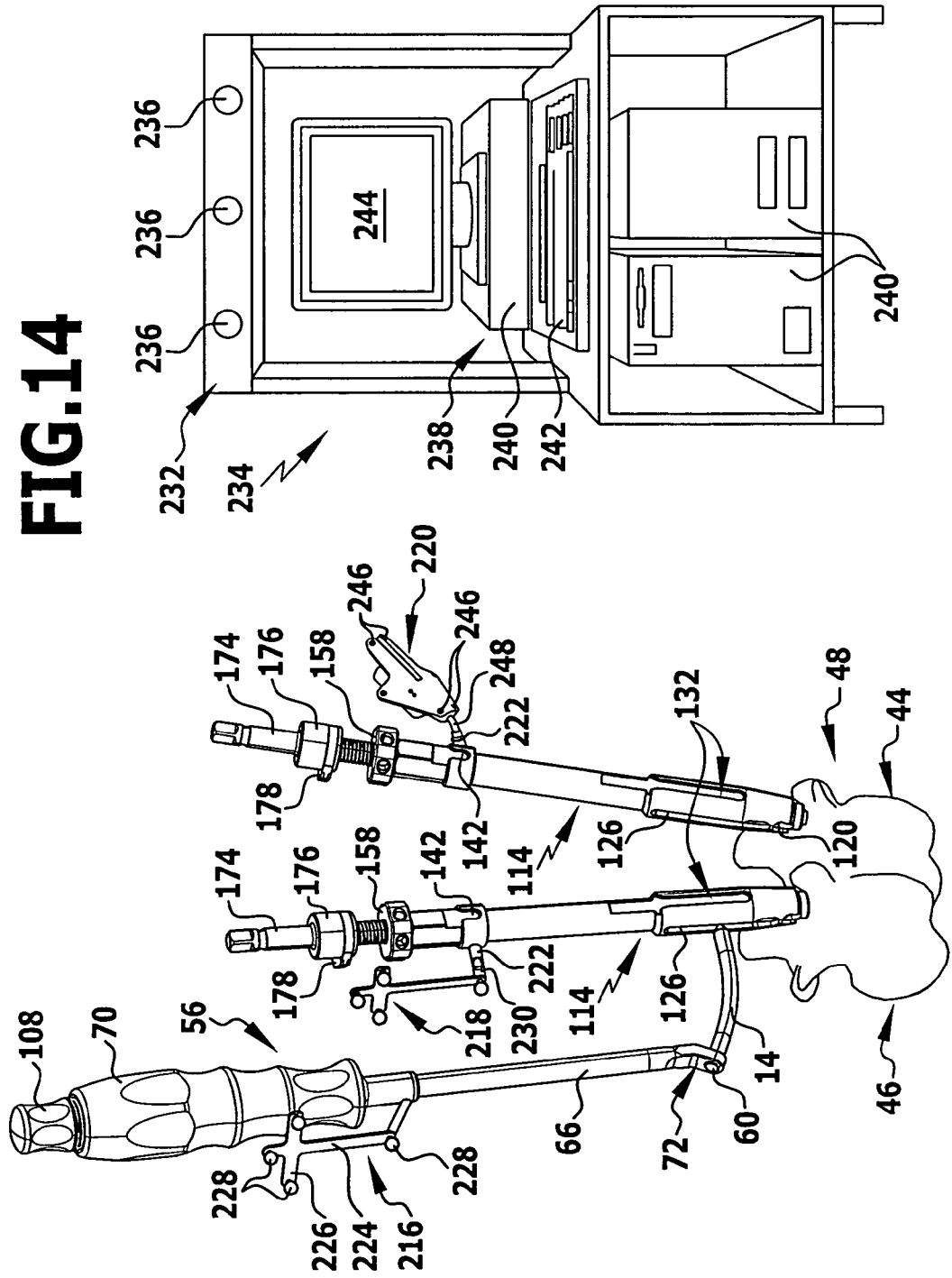
FIG. 14 is a perspective view similar to FIG. 14 with instruments provided for use in connection with a navigation system.

Optionally, both the rod insertion instrument 56 and the surgical instrument 114 can be equipped with reference elements 216, 218 and 220 which allow detection of a position and/or an orientation of the instruments 56 and 114 in a three-dimensional space defined, for example, by an operating theatre. The reference elements 216, 218 and 220 can be releasably connectable to the respective instrument 56 and 114. Preferably, an adapter 222 can be provided on the instrument, for example, on the projection 140 of the instrument 114 or on the shaft 66 of the instrument 56. However, it is also possible for the reference element to be connected unreleasably to the respective instrument 56 or 114. With reference to FIG. 14, the reference element 216, for example, is unreleasably connected to the shaft 66 of the instrument 56, whereas the reference elements 218 and 220 are releasably connected by means of the adapters 222, which are provided on the respective projection 140, to the instruments 114.

The reference elements 216, 218 and 220 shown in FIG. 14 are only examples. In principle, all commonly used and available reference elements could be connected to the instrument 56 and 114. For example, reference element 216 comprises two intersecting bars 224 and 226 which carry four small spheres 228 at their free ends. The spheres 228 are provided with a surface which is well-suited for reflecting electromagnetic radiation.

The reference element 218 is of the same type as reference element 216 but comprises an adapter 230 which corresponds to the adapter 222 so that the reference element 218 can be connected to the instrument 114. The spheres 228 form marker elements which can be detected by a detection device 232 of a navigation system. The detection device 232 comprises at least one transmitter or receiver 236 which is adapted to emit and/or receive radiation, for example, electromagnetic waves or ultrasound. An alternative for a detection device would be a device which is adapted to detect modifications or changes in of an electromagnetic field induced by the reference elements. The navigation system 234 further comprises a computer system 238 for calculation of the position and/or orientation of the reference element 216, 218 and 220 in the operating theatre and, therefore, determination of the position and the orientation of the instruments 56 and 114. The computer system 238 comprises at least one computer 240 with at least one commonly used input device, such as a keyboard 242, and a display 244 for displaying data processed by the computer system 238, for example, schemes or pictures indicating position and orientation of the instrument 56 and 114 in the operating theatre.

The reference element 220 is a reference element of an active type which is equipped with six active marker elements 246 for emitting radiation, for example, electromagnetic waves in the infrared region or ultrasound. Furthermore, the reference element 220 has an adapter 248 which corresponds to the adapter 222 provided on the instrument 114.

Of course, the reference elements can be changed as desired, for example, if the navigation system 234 is modified from a system using electromagnetic waves as carrier to a system using ultrasound as carrier. However, the reference element could also be constructed such that disturbances or changes in an electromagnetic field established in the operating theatre are detectable, which also allow detection of a position and/or an orientation of the respective reference element and, therefore, of the instrument to which the reference element is connected.

What is claimed is:

1. A surgical instrument for holding and inserting a connection member of an osteosynthesis device into a bone anchorage element, the instrument comprising a tubular body having a proximal end, a distal end, a first tubular section and a second tubular section adjacent to the first tubular section, the first tubular section having a first longitudinal axis, and the second tubular section having a second longitudinal axis extending transversely with respect to the first longitudinal axis, the tubular body forming a longitudinal bore extending through the first and second tubular sections, the second tubular section comprising a socket for receiving a connection member, the socket intersecting the longitudinal bore and having an longitudinal axis that extends transversely to the second longitudinal axis, the instrument further comprising a locking mechanism which is movable between a connection position to secure a connection member in the socket and a release position to release the connection member from the socket.

2. The surgical instrument according to claim 1, wherein the proximal end comprises a handle portion.

3. The surgical instrument according to claim 1, wherein the instrument is designed for torque proof connection with the connection member in the connection position.

4. The surgical instrument according to claim 1, wherein the locking mechanism comprises a locking member movably supported in the second tubular section.

5. The surgical instrument according to claim 4, wherein at least one stop is provided for limiting a movement of the locking member in distal direction.

6. The surgical instrument according to claim 4, wherein at least one stop is provided for limiting a movement of the locking member in proximal direction.

7. The surgical instrument according to claim 4, wherein a transmission member is provided for moving the locking member from the most proximal position to the most distal position.

8. The surgical instrument according to claim 7, wherein the transmission member is rotatably supported on the instrument.

9. The surgical instrument according to claim 7, wherein the transmission member comprises a distal end, the distal end of the transmission member being engageable with the locking member.

10. The surgical instrument according to claim 9, wherein the distal end of the transmission member abuts on a proximal end of the locking member.

11. The surgical instrument according to claim 7, wherein the transmission member defines a longitudinal axis, the locking member defines a longitudinal axis, and the longitudinal axis of the transmission member is inclined relative to the longitudinal axis of the locking member.

12. The surgical instrument according to claim 11, wherein an angle of inclination between the longitudinal axis of the transmission member and the longitudinal axis of the locking member lies in a range of from 100° to 170°.

13. The surgical instrument according to claim 7, wherein the transmission member comprises a distal end, and the distal end of the transmission member comprises the locking member.

14. The surgical instrument according to claim 4, wherein the locking member comprises at least one abutment surface facing in distal and/or proximal direction.

15. The surgical instrument according to claim 14, wherein the locking member comprises a peripheral groove, and the at least one abutment surface is formed by side walls of the peripheral groove.

16. The surgical instrument according to claim 15, wherein the at least one stop comprises an inwardly pointing projection extending at least partially into the peripheral groove.

17. The surgical instrument according to claim 1, wherein a hollow shaft extending between the second tubular section and the proximal end is provided.

18. The surgical instrument according to claim 17, wherein the transmission member is movably supported on the shaft.

19. The surgical instrument according to claim 17, wherein the transmission member is directly or indirectly threadingly engaged with the shaft or a part thereof.

20. The surgical instrument according to claim 17, wherein the transmission member comprises a first threaded section, and the shaft comprises a second threaded section corresponding to the first threaded section for allowing a movement of the transmission member in distal or proximal direction in response to a turning movement about a longitudinal axis of the transmission member.

21. The surgical instrument according to claim 20, wherein the second threaded section is provided in the form of an internal thread of the shaft in a section adjacent to the connection portion.

22. The surgical instrument according to claim 17, wherein the locking member is guided in the distal end of the shaft.

23. The surgical instrument according to claim 1, wherein an actuation member is provided, said actuation member being arranged at the proximal end and being operatively connected with the locking member in such a way that actuation of the actuation member results in a movement of the locking member in a distal and/or proximal direction.

24. The surgical instrument according to claim 23, wherein the actuation member is operatively connected to the transmission member.

25. The surgical instrument according to claim 24, wherein the actuation member is connected in a torque proof manner to the transmission member.

26. The surgical instrument according to claim 23, wherein the actuation member comprises a turning knob arranged at a proximal end of the instrument.

27. The surgical instrument according to claim 23, wherein the transmission member comprises a proximal end, the actuation member being connected to the proximal end of the transmission member.

28. The surgical instrument according to claim 1, wherein the socket comprises a through-hole for receiving the connection member.

29. The surgical instrument according to claim 28, wherein the through-hole is arranged in a direction transverse to a longitudinal axis defined by the instrument section on which the through-hole is arranged.

30. The surgical instrument according to claim 28, wherein the through-hole has a cross section of a non-circular shape.

31. The surgical instrument according to claim 30, wherein the cross section is of polygonal shape.

32. The surgical instrument according to claim 1, wherein the instrument further comprises the connection member.

33. The surgical instrument according to claim 32, wherein the connection member is designed in the form of a rod.

34. The surgical instrument according to claim 32, wherein the connection member is curved.

35. The surgical instrument according to claim 32, wherein the connection member has a circular cross section.

36. The surgical instrument according to claim 32, wherein the connection member has connection portion which is connectable with the second tubular section in the connection position.

37. The surgical instrument according to claim 36, wherein the connection portion is arranged at a first free end of the connection member.

38. The surgical instrument according to claim 36, wherein the at connection portion forms a first free end of the connection member.

39. The surgical instrument according to claim 36, wherein the connection portion has a non-circular cross section.

40. The surgical instrument according to claim 39, wherein the connection portion has a polygonal cross section.

41. The surgical instrument according to claim 40, wherein the connection portion has a hexagonal cross section.

42. The surgical instrument according to claim 36, wherein the second tubular section and the connection portion of the connection member are dimensioned such that they have play when the connection portion is inserted into the second tubular section in the release position and that the play is eliminated in the locking position by means of the locking mechanism.

43. The surgical instrument according to claim 32, wherein the connection member has at least a second end which is designed in the form of an edge-free tip.

44. The surgical instrument according to claim 43, wherein the edge-free tip is blunt.

45. The surgical instrument according to claim 43, wherein the first longitudinal axis runs transverse relating to a direction defined by the at least one second end.

46. The surgical instrument according to claim 1, wherein an irrigation adapter is provided at the proximal end, the adapter being connectable to an irrigation source by means of a hose and being in fluid communication with the interior of the shaft.

47. The surgical instrument according to claim 1, wherein a reference element is provided on the instrument, the reference element being constructed such that it is detectable by a detection device of a navigation system.

48. The surgical instrument according to claim 47, wherein the reference element is releasably connectable to the instrument.

49. A surgical instrument for holding and inserting a connection member of an osteosynthesis device into a retainer of a bone anchorage element, the instrument comprising a distal end, a proximal end and a first connection portion at the distal end, the first connection portion comprising a connection member receptacle for receiving at least a portion of the connection member, the instrument further comprising a locking mechanism which is transferable from a release position, in which the instrument is releasable from the connection member, to a connection position, in which the instrument can be connected to the connection member, the locking mechanism comprising a locking member movably supported on the first connection portion, wherein the locking member is biased in a proximal direction.

50. The surgical instrument according to claim 49, wherein a bias member is provided for biasing the locking member in proximal direction.

51. An osteosynthesis device comprising at least two bone anchorage elements and at least one connection member, further comprising a surgical instrument for holding and inserting the connection member into at least one retainer of the bone anchorage elements, the instrument comprising a tubular body having a proximal end, a distal end, a first tubular section and a second tubular section adjacent to the first tubular section, the first tubular section having a first longitudinal axis, and the second tubular section having a second longitudinal axis extending transversely with respect to the first longitudinal axis, the tubular body forming a longitudinal bore extending through the first and second tubular sections, the second tubular section comprising a socket for receiving a connection member, the socket intersecting the longitudinal bore and having an longitudinal axis that extends transversely to the second longitudinal axis, the instrument further comprising a locking mechanism which is movable between a connection position to secure a connection member in the socket and a release position to release the connection member from the socket.

52. The osteosynthesis device according to claim 51, wherein the at least two bone anchorage elements comprise at least one bone screw having a U-shaped receptacle for receiving at least a part of the at least one connection member, the at least one bone screw comprising a fixing element for securing the at least one connection member in the receptacle in a connection position.

53. The osteosynthesis device according to claim 51, wherein the proximal end comprises a handle portion.

* * * * *